United States Patent
Adler et al.

(10) Patent No.: US 10,864,032 B2
(45) Date of Patent: Dec. 15, 2020

(54) FLUID CONNECTING SYSTEM AND CRYOPROBE WITH SAME

(71) Applicant: Erbe Elektromedizin GmbH, Tuebingen (DE)

(72) Inventors: Marcus Adler, Tuebingen (DE); Hanna Andel, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 396 days.

(21) Appl. No.: 15/891,901

(22) Filed: Feb. 8, 2018

(65) Prior Publication Data
US 2018/0228526 A1    Aug. 16, 2018

(30) Foreign Application Priority Data

Feb. 10, 2017  (EP) .................................. 17155740

(51) Int. Cl.
*B29C 65/54* (2006.01)
*A61B 18/02* (2006.01)
(Continued)

(52) U.S. Cl.
CPC .......... *A61B 18/02* (2013.01); *B29C 65/1406* (2013.01); *B29C 65/1435* (2013.01); *B29C 65/4845* (2013.01); *B29C 65/548* (2013.01); *B29C 66/1222* (2013.01); *B29C 66/1224* (2013.01); *B29C 66/322* (2013.01); *B29C 66/5221* (2013.01); *B29C 66/52292* (2013.01); *B29C 66/52293* (2013.01); *B29C 66/5344* (2013.01); *A61B 2017/00017* (2013.01); *A61B 2018/00172* (2013.01); *A61B 2018/0212* (2013.01); *A61B 2018/0262* (2013.01);
(Continued)

(58) Field of Classification Search
CPC ... F16L 39/02; B29C 65/548; B29L 2023/007
USPC ........................................... 285/294.3, 123.3
See application file for complete search history.

(56) References Cited

U.S. PATENT DOCUMENTS

| | | | |
|---|---|---|---|
| 3,439,680 A | 4/1969 | Thomas, Jr. | |
| 3,536,075 A | 10/1970 | Thomas, Jr. | |

(Continued)

FOREIGN PATENT DOCUMENTS

| | | | |
|---|---|---|---|
| CN | 1038410 A | 1/1990 | |
| CN | 1846644 A | 10/2006 | |

(Continued)

OTHER PUBLICATIONS

Search Report in corresponding European Application No. 17155740.8, dated Jul. 20, 2017, 7 pages.

(Continued)

*Primary Examiner* — David Bochna
(74) *Attorney, Agent, or Firm* — Fitch, Even, Tabin & Flannery LLP

(57) ABSTRACT

The fluid connecting system comprises a connecting piece (16) that consists of a single injection-molded part of plastic material, said part accommodating a coaxial first fluid conveying arrangement (15), as well as an also coaxial second fluid conveying arrangement (17) and providing several adhesive reservoirs that allow a pressure-resistant gluing of the two fluid conveying arrangements (15, 17) to each other by a reliable safe process.

19 Claims, 7 Drawing Sheets

(51) Int. Cl.
    *B29C 65/14*     (2006.01)
    *B29C 65/48*     (2006.01)
    *B29C 65/00*     (2006.01)
    *A61B 18/00*     (2006.01)
    *B29L 23/00*     (2006.01)
    *A61M 25/00*     (2006.01)
    *A61B 17/00*     (2006.01)
    *F16L 39/00*     (2006.01)

(52) U.S. Cl.
    CPC ............. *A61M 2025/0039* (2013.01); *B29L 2023/007* (2013.01); *F16L 39/00* (2013.01)

(56) References Cited

U.S. PATENT DOCUMENTS

| | | | |
|---|---|---|---|
| 3,841,671 A * | 10/1974 | Walker | F16L 39/02 |
| | | | 285/148.21 |
| 7,000,644 B2 * | 2/2006 | Ichimura | F16L 39/02 |
| | | | 138/109 |
| 2003/0028182 A1 | 2/2003 | Abboud et al. | |
| 2005/0055017 A1 | 3/2005 | Damasco et al. | |
| 2007/0191732 A1 | 8/2007 | Voegele | |
| 2007/0241560 A1 * | 10/2007 | Malone | F16L 37/56 |
| | | | 285/319 |
| 2011/0152851 A1 | 6/2011 | Formica | |
| 2013/0023770 A1 | 1/2013 | Courtney et al. | |
| 2013/0207383 A1 * | 8/2013 | Sixsmith | F16L 39/005 |
| | | | 285/123.3 |
| 2015/0190196 A1 | 7/2015 | Jimenez et al. | |
| 2015/0202004 A1 | 7/2015 | Bonn et al. | |
| 2016/0074089 A1 | 3/2016 | Moreau et al. | |
| 2016/0302867 A1 | 10/2016 | Willyard et al. | |
| 2017/0336008 A1 * | 11/2017 | Hankins | B29C 65/542 |

FOREIGN PATENT DOCUMENTS

| | | |
|---|---|---|
| CN | 101015473 A | 8/2007 |
| CN | 101188977 A | 5/2008 |
| CN | 102065785 A | 5/2011 |
| CN | 204797985 U | 11/2015 |
| CN | 105361949 A | 3/2016 |
| CN | 105920717 A | 9/2016 |
| CN | 105943159 A | 9/2016 |
| CN | 106264707 A | 1/2017 |
| CN | 106264721 A | 1/2017 |
| EP | 0428976 A1 | 5/1991 |
| EP | 1003430 B1 | 11/2004 |
| EP | 1707150 A2 | 10/2006 |
| EP | 3127575 A2 | 2/2017 |
| WO | 8908471 A1 | 9/1989 |
| WO | 2012018439 A1 | 2/2012 |
| WO | 2015066521 A1 | 5/2015 |

OTHER PUBLICATIONS

Chinese First Office Action and Search Report dated Apr. 16, 2020, in corresponding Chinese Application No. 201810135300.9, with English translation (22 pages).

* cited by examiner

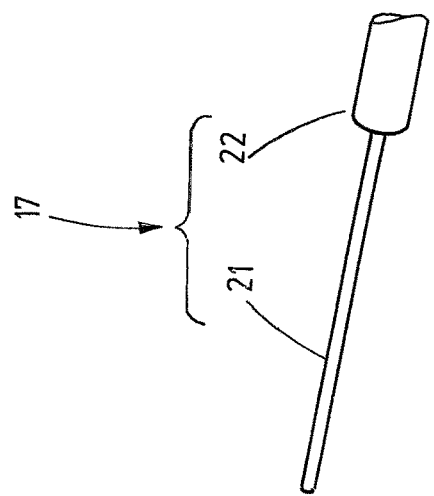
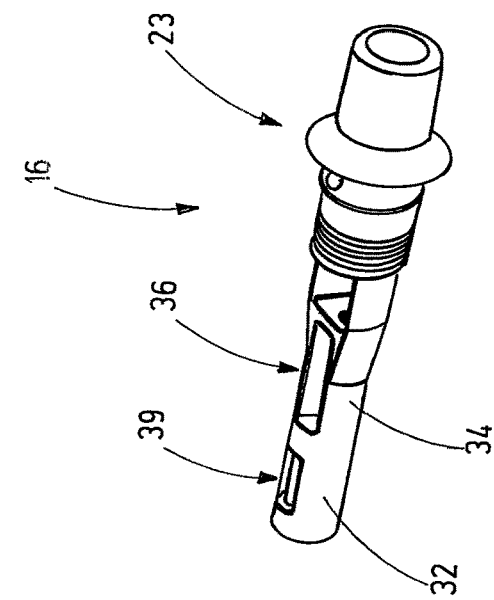
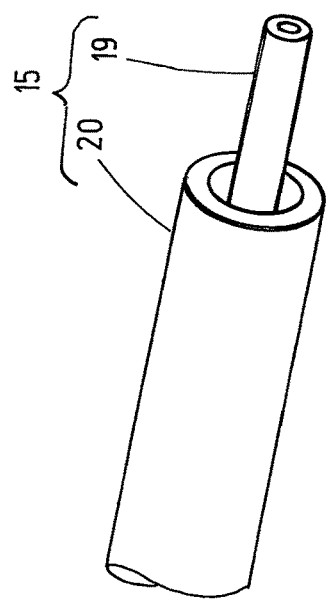
Fig.3

FLUID CONNECTING SYSTEM AND CRYOPROBE WITH SAME

RELATED APPLICATION(S)

This application claims the benefit of European Patent Application No. EP 17155740.8 filed Feb. 10, 2017, the contents of which are incorporate herein by reference as if fully rewritten herein.

TECHNICAL FIELD

The invention relates to a fluid connecting system for connecting two coaxial lines to each other, in particular for cryoprobes. Furthermore, the invention relates to a cryoprobe equipped with a fluid connecting system according to the invention.

BACKGROUND

In the case of cryoprobes and other medical instruments that must be supplied with fluids, for example fluids or gasses, the connection of supply lines to the appropriate applicator lines is frequently necessary.

Regarding this, publication U.S. Pat. No. 3,439,680 describes a handpiece on whose proximal end the supply lines and on whose distal end the applicator lines of a cryoprobe are connected. The handpiece thus forms a shunt provided with appropriate fluid channels that are disposed on their distal end for the accommodation of a probe with coaxial lines and on their proximal end for the connection of lines that are arranged parallel thereto.

The system known from publication U.S. Pat. No. 3,536,075 satisfies the same principle, said system again comprising a handpiece with a proximal line-parallel connection and a distal coaxial connection.

Such instruments are suitable for open surgical applications, wherein the instrument is guided manually on the handle and wherein the handle can form a shunt. These devices are not suitable for laparoscopic or endoscopic applications.

It is the object of the invention to provide a fluid connecting system that is suitable for instruments, probes or the like that are suitable for endoscopic applications. Furthermore, it is the object of the invention to provide an appropriately suitable cryoprobe.

The fluid connecting system according to the invention forms a mechanical and fluid-permeable connection between a first fluid conveying arrangement and a second fluid conveying arrangement. These two fluid conveying arrangements have the same or also—typically—different diameters. Each coaxial fluid conveying arrangement comprises an inner line and an outer line, wherein the respective inner line extends through the inner lumen of the respective outer line. The fluid conveying arrangement is referred to as "coaxial" even if the inner line is arranged off-center in the lumen of the outer line along its entire length or parts thereof—extending through the lumen, in any event. In typical applications, the fluid flows in the inner lines in distal direction; in the outer lines it flows in proximal direction and thus counter-directionally. The directions of flow may also occur in reverse direction, in which case the description and claims hereinafter apply analogously.

In the fluid connecting system according to the invention, the end of the outer line extends beyond the end of the inner line in the case of the first fluid conveying arrangement. The second fluid conveying arrangement is arranged distally with respect to the first fluid conveying arrangement. In the second fluid conveying arrangement the proximal end of the inner line projects from the proximal end of the outer line. Each of the ends of the two outer lines is connected to an outer line socket.

Preferably, the ends of the inner lines are directly connected and held in an inner line socket. The inner line socket and the outer line socket are connected to each other via a spacer. The outer line socket, the inner line socket and the spacer form a connecting piece that may be configured as a one-piece injection-molded plastic part The inner line socket and the outer line socket are spaced apart in axial direction. At the same time, the overlap of the ends of the outer lines and the overlap of the ends of the inner line are spaced apart in axial direction.

This arrangement represents an extremely slim design and is suitable, in particular, for connecting fluid conveying arrangements having different outside diameters. Preferably, the distal, i.e., the second fluid conveying arrangement, has a smaller outside diameter than the first, i.e., proximal fluid conveying arrangement. In particular, the diameter difference allows a very slim design for the use in catheters for the distal cryoprobe, on the one hand, and the proximal fluid conveying arrangement may have a sufficiently large diameter, on the one hand, in order to make possible favorable flow conditions, in particular a low flow resistance.

The concept of connection used in both fluid conveying arrangements preferably assumes that the outer lines are indirectly connected to each other via the outer line socket, and the inner lines are directly connected to each other. For connecting the first, i.e., proximal return line, the outer line socket has an outside peripheral surface that forms a seat that accommodates the first outer line. The seat may be structured and, accordingly, have ribs, projections, recesses and the like. In particular, the first outer line can be glued to the outer peripheral surface of the outer line socket. The glued connection is preferably achieved with an adhesive by curing, for example with UV light, said curing being initiated externally.

Preferably, the outer line socket has an opening in which the second, i.e., distal, outer line is held. Preferably, this outer line is glued to the inner surface of the opening. The outer line socket may have a passage that extends from the outer peripheral surface to the inner surface of the opening and preferably acts as the adhesive reservoir. In doing so, the two outer lines can be connected to each other by a simple process in a pressure-resistant and process-reliable manner by being glued to the outer line socket. When the connection is being established after the insertion of the second fluid conveying arrangement in the outer line socket, the passage and the adhesive reservoir, respectively, are filled with adhesive, in which case the adhesive migrates—due to capillary forces—into the joining gap between the second outer line and the outer line socket. To accomplish this, the joining gap and the adhesive are adapted to each other in such a manner that the joining gap is filled with adhesive due to the existing capillary forces along the entire circumference of the passage opening and along its entire length.

During the assembly, sufficient adhesive may be filled in the adhesive reservoir so that the adhesive—irrespective of any potential production tolerances—is sufficient, at any rate, for filling the gap between the outer line socket and the second outer line, this contributing to the safe process of establishing the adhesive connection. Furthermore, it can also wet the peripheral surface, so that the outer line slipped onto said peripheral surface will be bonded to the outer peripheral surface as soon as the adhesive has cured. Alternatively, the adhesive may be applied separately to the outer peripheral surface, e.g. to a region provided with grooves extending in peripheral direction.

In doing so, the axial arrangement and the expansion of the outer lines are preferably such that the end of the second outer line extends into the first outer line, i.e., the ends of both outer lines overlap. In particular, the adhesive reservoir is arranged between the inner surface of the first fluid conveying line and the outer surface of the second outer line as a result of this, this, in turn, contributing to the safe process of providing the adhesive connection. The outer line socket bridges the outer lines given by the diameter differences.

The inner lines of the two fluid conveying arrangements are preferably also directly glued to each other, in which case, to accomplish this, preferably the proximal end of the second inner line extends into the distal end of the first inner line, i.e., the end of the second inner line is received by the end of the first inner line. Preferably, the distal end of the first inner line is held in an inner line socket that belongs to the connecting piece and is connected—via the spacer—to the outer line socket that also belongs to the spacer.

For the accommodation of the first inner line, the inner line socket has a tubular seat that is provided with a preferably radially oriented adhesive filling opening that communicates with the outer surface of the first inner line. Adhesive that is injected here connects the tubular seat to the outer surface of the first inner line in that said adhesive enters into a capillary gap that is formed between the tube-like seat of the inner line socket and the inner line.

Preferably, the inner line socket has a second adhesive filling opening. It is formed, e.g., by the edge of an adhesive-receiving well through which extends the second inner line. This well is adjacent to the tubular seat and arranged on the side of the inner line socket facing the outer line socket. The well forms an adhesive reservoir from which the adhesive may penetrate into an intermediate space formed between the outer surface of the second inner line and the inner surface of the first inner line. Preferably, the width of the gap is such that a capillary gap is formed into which the adhesive may penetrate or be drawn. The adhesive connection between the two inner lines is thus possible in a simple and safe process, in that, after the insertion of the inner lines in the connecting body, adhesive is filled into the adhesive filling opening.

The inner line socket is preferably connected to the outer line socket by means of a spacer that creates a distance between the outer line socket and the inner line socket. Due to this distance, the fluid connection between the two outer lines is possible. This concept allows the connecting piece to be manufactured without offsets, so that it can be produced in a particularly simple manner in the form of a finished injection-molded part of plastic material.

BRIEF DESCRIPTION OF THE DRAWINGS

Additional details of advantageous embodiments of the invention are the subject matter of the description or the drawings. The individual features of the described embodiments may be of inventive importance when taken out of the overall context. The drawings show:

FIG. 3 an exploded view of the fluid connecting system according to FIG. 2, prior to assembly;

DETAILED DESCRIPTION

Figure 1:
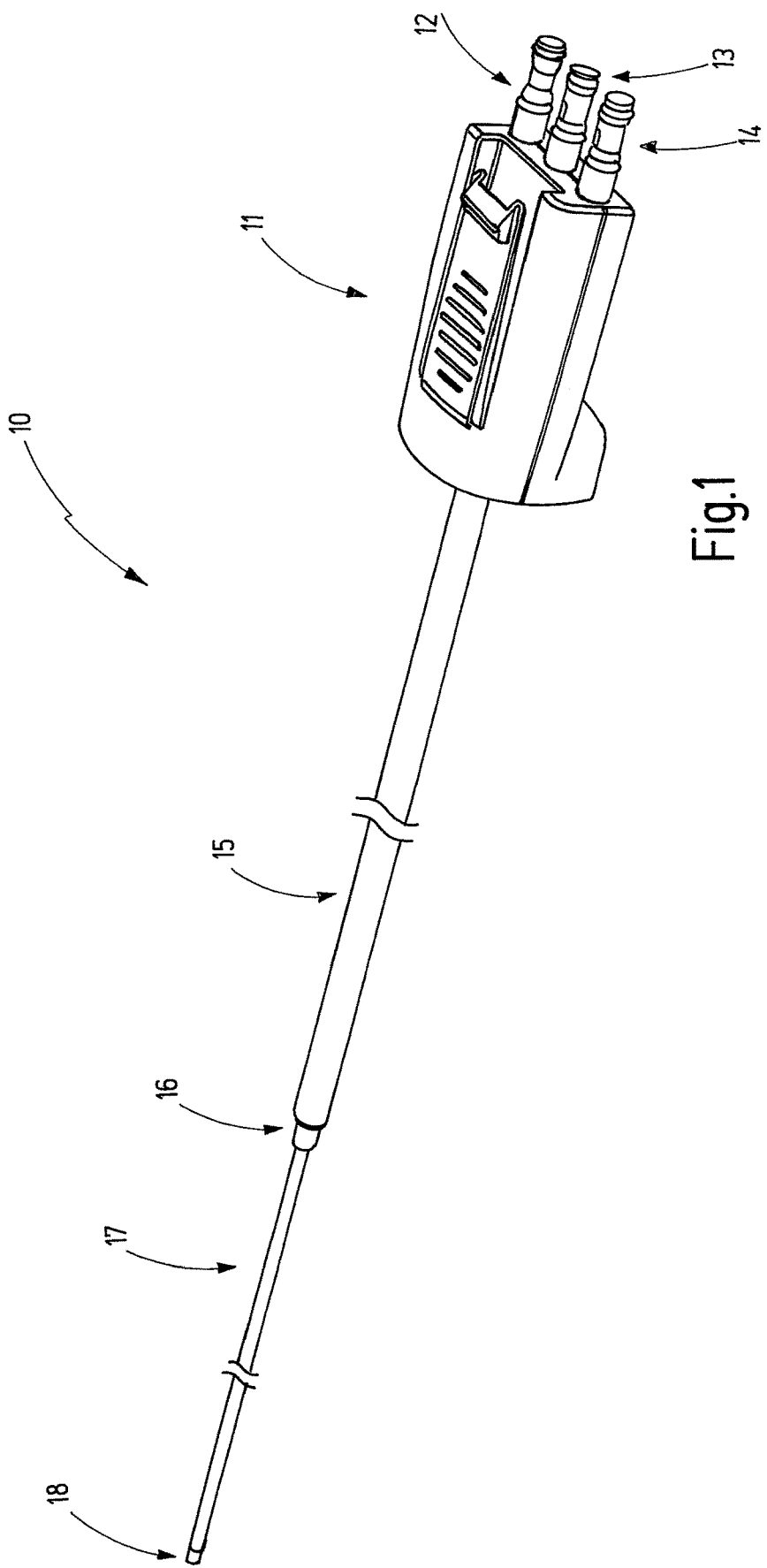
FIG. 1 a greatly abbreviated perspective representation of a cryoprobe according to the invention with a fluid connecting system between the distal probe part and the proximal fluid supply.

FIG. 1 shows a cryoprobe 10 that is disposed for use in endoscopic applications. Proximally, the cryoprobe 10 comprises a fluid plug 11 with plug pins 12, 13, 14, by way of which liquid or gaseous fluids can be supplied or discharged. Starting from the fluid plug 11, there is a coaxial fluid conveying arrangement 15 leading to a fluid connecting system that preferably is represented by a connecting piece 16. A second fluid conveying arrangement 17 extends away from the connecting piece 16 in distal direction. On the distal end of the second fluid conveying arrangement 17 there is provided an effector, for example a cryo head 18. The illustration of FIG. 1 is not true to scale—the length of the first fluid conveying arrangement 15 may be up to several meters. Also, the length of the second fluid conveying arrangement may be considerable and range from a few decimeters to more than one meter. The specific length depends on the desired situation of application.

Figure 2:
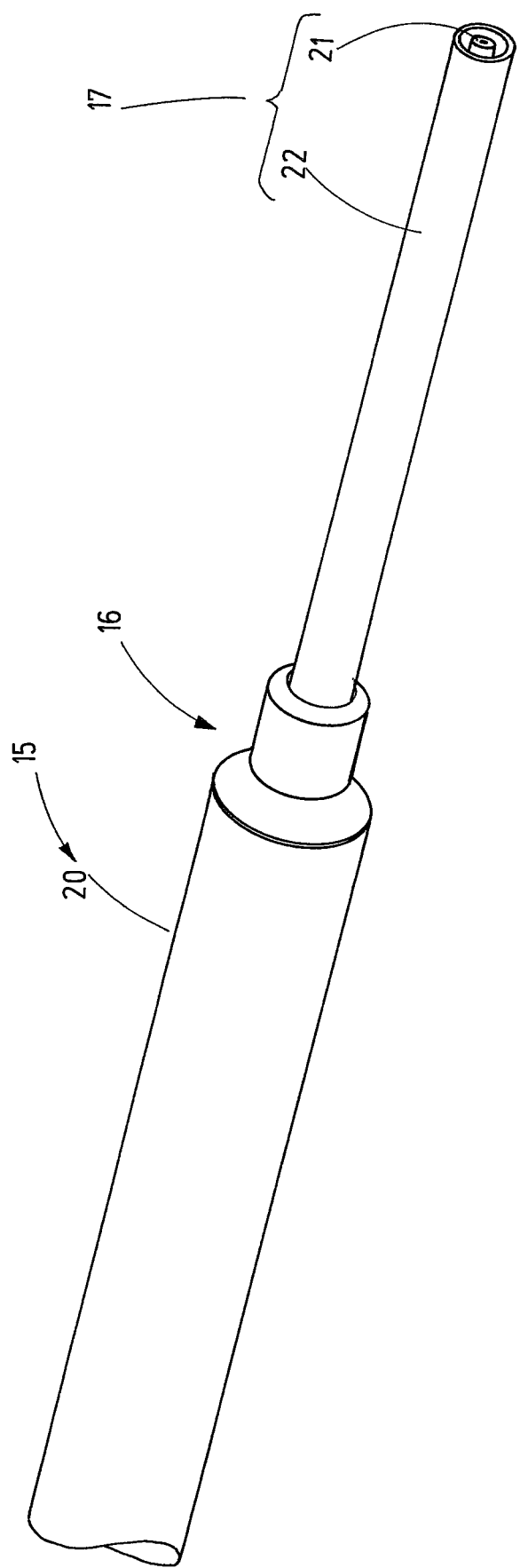
FIG. 2 a perspective representation from a different viewing direction of the fluid connecting system of the cryoprobe according to FIG. 1.

The two fluid conveying arrangements 15, 17 are coaxial arrangements, as can be inferred from FIGS. 2 and 3. The first fluid conveying arrangement 15 comprises a first inner line 19 and a first outer line 20, the latter preferably consisting of UV-permeable plastic. In the fluid conveying arrangement 15, the inner line 19 extends through the lumen of the outer line 20, in which case the diameter of the lumen of the outer line 20 is substantially greater than the outside diameter of the first inner line 19. The inner line 19 is placed with play inside the lumen of the first outer line 20. Even if the inner line 19 were not centered in the outer line, this would still be referred to as a coaxial arrangement.

Analogously, this applies to the second fluid conveying arrangement 17 that comprises a second inner line 21 and a second outer line 22 that are arranged so as to be coaxial relative to each other. This means that the second inner line 21 extends through the lumen of the second outer line 22, without needing to extend in a precisely centered manner. There is a distance between the outer surface of the second inner line 21 and the inner surface of the second outer line 22, so that the existing annular space may act as a fluid return.

The first inner line 19 is connected to one of the plug pins 12 to 14 of the fluid plug 11. The first fluid conveying line 20 is connected to another of the plug pins 12 to 14. The free flow cross-sections of the first inner line 19 and the first outer line 20 are substantially greater than the free flow cross-sections of the second inner line 21 and the second outer line 22. Likewise, the outside diameter of the second fluid conveying arrangement 17 is preferably smaller than the outside diameter of the first fluid conveying arrangement 15.

Figure 4:
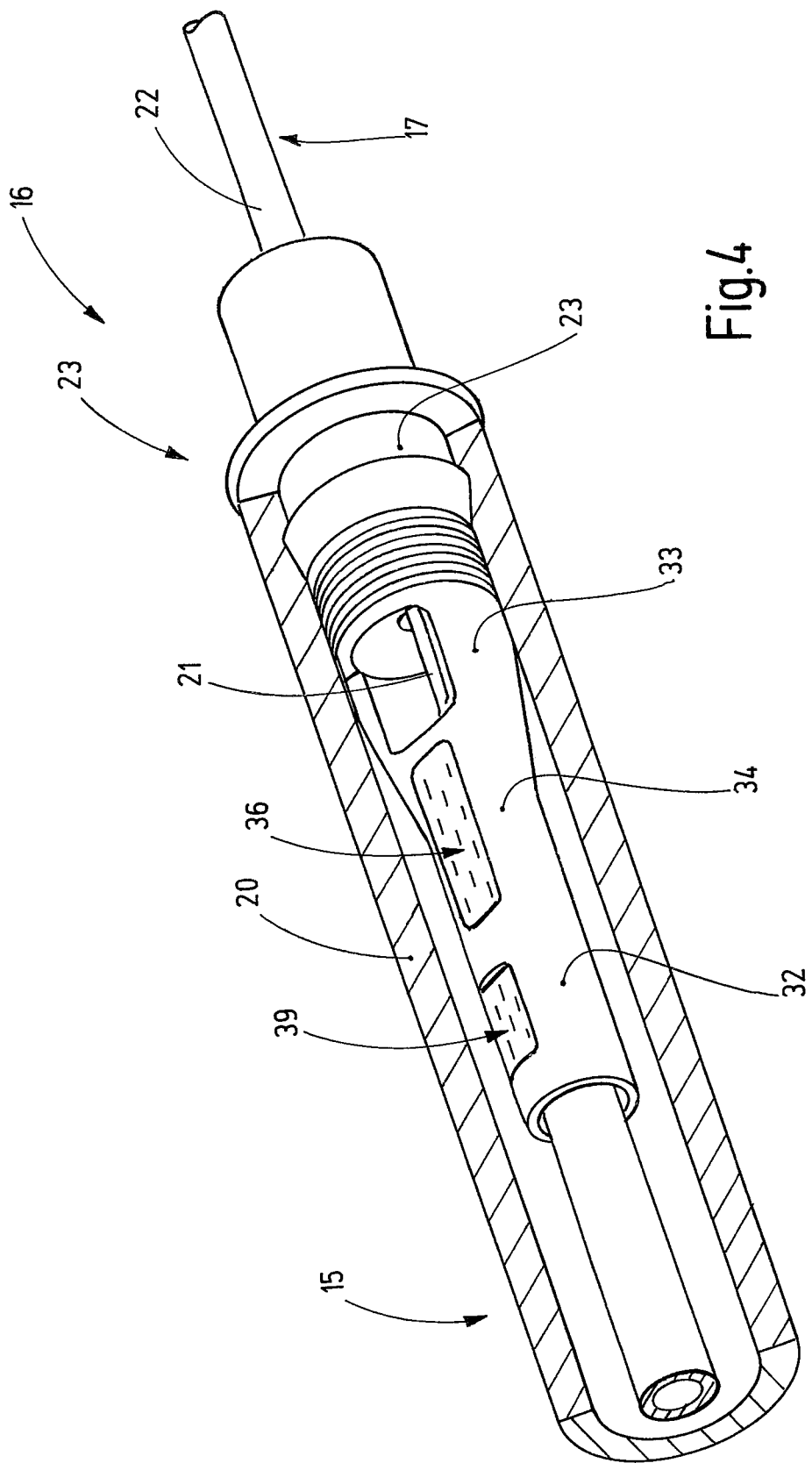
FIG. 4 a perspective view, partially in section, of the fluid connecting system according to FIGS. 2 and 3.
Figure 5:
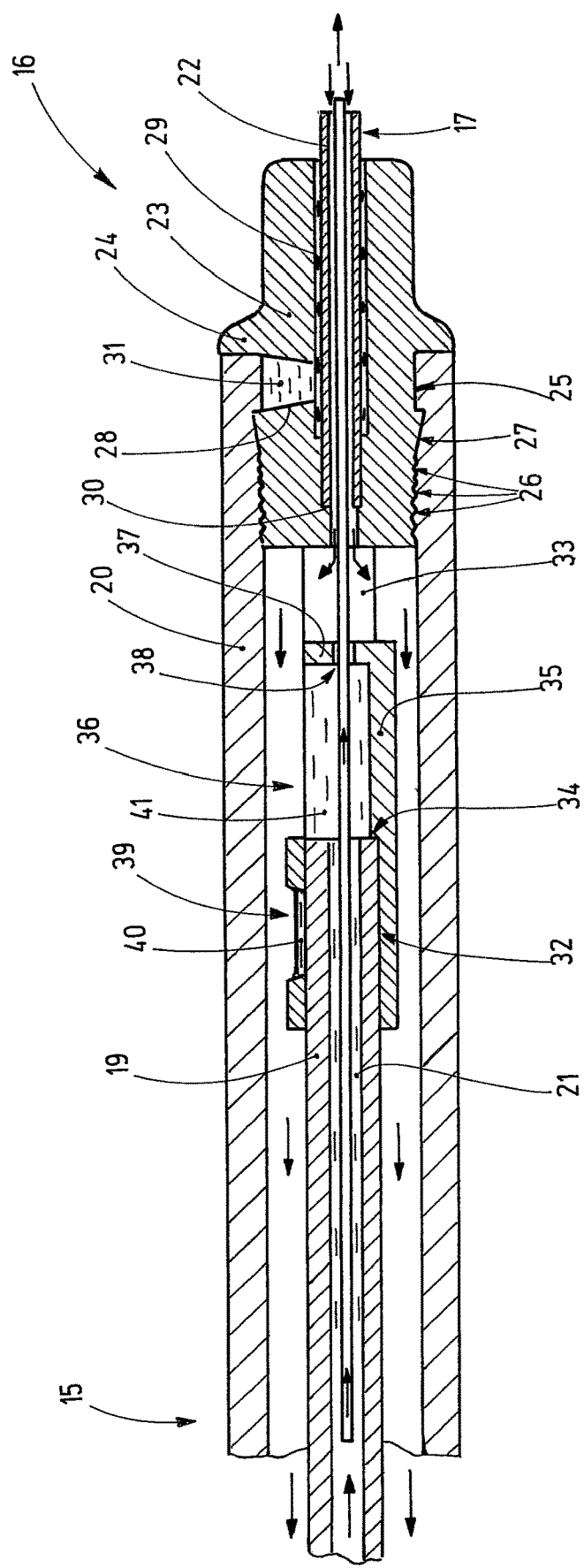
FIG. 5 a longitudinal section of the fluid connecting system according to FIGS. 2 to 4.

The fluid connecting system can be inferred from FIG. 3, prior to assembly, and from FIGS. 4 and 5, after assembly. As is obvious, this system is preferably represented by the connecting piece 16 consisting preferably of UV-permeable plastic, said connecting piece having a connector-like section that represents one outer line socket 23. It has a collar 24 that delimits an outer peripheral surface 25 terminating on the collar, said surface forming a seat for the first outer line 20. The outer peripheral surface 25 may be cylindrical or, as depicted, structured, in that it has several—preferably peripheral, grooves 26 as well as, optionally, one or more ribs 27, whose sawtooth profile allows that the outer line 20 can be slipped onto the outer peripheral surface 25 that, however, resists a pulling off of said outer line.

Starting from the outer peripheral surface 25, there extends a radial passage 28 to an axial passage opening 29 that accommodates the second outer line 22 and a seat for these. The passage opening 29 extends up to a step 30 where the diameter of the passage opening 29 decreases slightly. The decreased inside diameter, however, is substantially greater than the outside diameter of the second inner line 21, and is preferably at least as large as the inside diameter of the second outer line 22. In assembled state, the proximal face of the second outer line 22 abuts against this step, and the second inner line extends—with radial play—through the passage opening 29.

A capillary gap is formed between the inner surface of the passage opening 29 and the outer surface of the second outer line 22, the width of said gap being dimensioned such that curable adhesive filled into the passage 28 migrates into the resultant gap and forms a meniscus on the face-side distal end of the passage opening 29, without leaking out.

As is obvious, the step 30—when viewed from the distal direction—is arranged beyond the passage 28, so that the passage 28 extends from the inner side of the first outer line 20 and extends to the outside of the second outer line 22. The passage 28 is located between the step 30 and the collar 24. In other words: the end of the second outer line 22 is plugged into the first outer line 20. Adhesive 31 filled into the passage 28 also wets the outer peripheral surface 25 and, optionally, the grooves 26, so that—in joined condition—an adhesive bond is formed between the first outer line 20 and the second return line 22 with the outer line socket 23 of the fluid connecting system 16 being interposed.

The second inner line 21 projects from the proximal end of the second outer line 22 and extends up to and into the distal end of the first inner line 19 that itself is clearly overlapped by the first outer line 20. The distal end of the first inner line 19 is received by an inner line socket 32 that is connected to the outer line socket 23 via one or more spacers 33.

The inner line socket 32 is formed by a tube-like section whose inside diameter is minimally greater than the outside diameter of the first inner line 19. The tube-shaped section of the inner line socket 32 transitions on an annular shoulder 34 into a well section 35 that has an adhesive filling opening 36 and is closed by a wall 37 in the direction toward the spacer 33. This wall has an opening 38 with a diameter that is preferably greater than the diameter of the second inner line 21. Preferably the diameter of the opening 38 is at least as large as the inside diameter of the annular shoulder 34. As a result of this, a particularly simple injection-molding tool for the production of the connecting piece 16 in the form of an injection-molded part can be designed. The second inner line 21 extends through this opening 38 and through the well section 35, as well as into or through the inner line socket 32.

The inner line socket 32 has at least preferably one adhesive filling opening 39 that extends through the wall of the tubular inner line socket 32 in radial direction and is preferably adjacent to the adhesive filling opening 36.

Between the inner surface of the inner line socket 32 and the outer surface of the first inner line 19, there is preferably formed a capillary gap having a width such that adhesive is drawn into the capillary gap, without leaking out. Preferably, the adhesive forms an appropriate meniscus on the proximal face of the inner line socket 32. Likewise, the inside diameter of the first inner line 19 and outside diameter of the second inner line 21 are adapted to each other in such a manner that the cylindrical annular gap takes up adhesive provided in the well section 35, without said adhesive reaching or closing the proximal end of the second inner line 21.

Regarding its diameter, the opening 38 is advantageously dimensioned in such a manner than an uncontrolled leaking of the adhesive 41 out of the wall section 35 after it has been filled with liquid adhesive will not occur.

The fluid connecting system 16 described so far hereinabove is manufactured as explained with reference to FIGS. 3 and 4:

Referring to the fluid connecting system according to FIG. 3, first the second fluid conveying arrangement 17 is inserted until the second inner line 21 projects through the inner line socket 32 and the second outer line 22 abuts against the step 30. Thereafter, the first fluid conveying arrangement 15 is attached to the fluid connecting system in that the first inner line 19 is slipped onto the second inner line 21 and into the inner line socket 32 up to the stop formed by the annular shoulder 34. Now the adhesive 31, 40, 41 is filled into the passage 28 and into the adhesive filling openings 36, 39. In doing so, the adhesive wets the inner surface of the passage opening 29, as well as the outer surface of the second outer line 22. Furthermore, the adhesive 40 wets the outer surface of the first inner line 19 and the inner surface of the inner line socket 32. The adhesive 41 injected via the adhesive filling opening 36 wets the outer surface of the second inner line 21 and penetrates into the intermediate space between the two inner lines 19, 21. Additional adhesive is applied to the grooves 26 and the outer peripheral surface 25, respectively, whereupon the first outer line 20 is slipped onto the outer peripheral surface 25. Then curing of the adhesive 31, 40, 41 is initiated. Preferably, this can be accomplished by UV radiation. To do so, the first outer line 20 and/or the fluid connecting system, i.e., the plastic of which this injection-molded part consists, is made so as to be permeable to UV light and/or conduct UV light.

After curing the adhesive, a durable, firm, pressure-resistant connection is formed between the first fluid conveying arrangement 15 and the second fluid conveying arrangement 17.

The fluid connecting system according to the invention consists of a single injection-molded part of plastic that accommodates a coaxial first fluid conveying arrangement 15, as well as an also coaxial second fluid conveying arrangement 17, and provides several reservoirs for adhesives that allow a pressure-resistant safe process for bonding the two fluid conveying arrangements 15, 17 to each other. The fluid connecting system is distinguished by a high functional integration in only one component, namely the connecting piece 16. Furthermore, with the use of the connecting piece 16 and the adhesive connection, a connection of the two fluid conveying arrangements 15, 17 displaying mechanical tensile strength is achieved.

Figure 6:
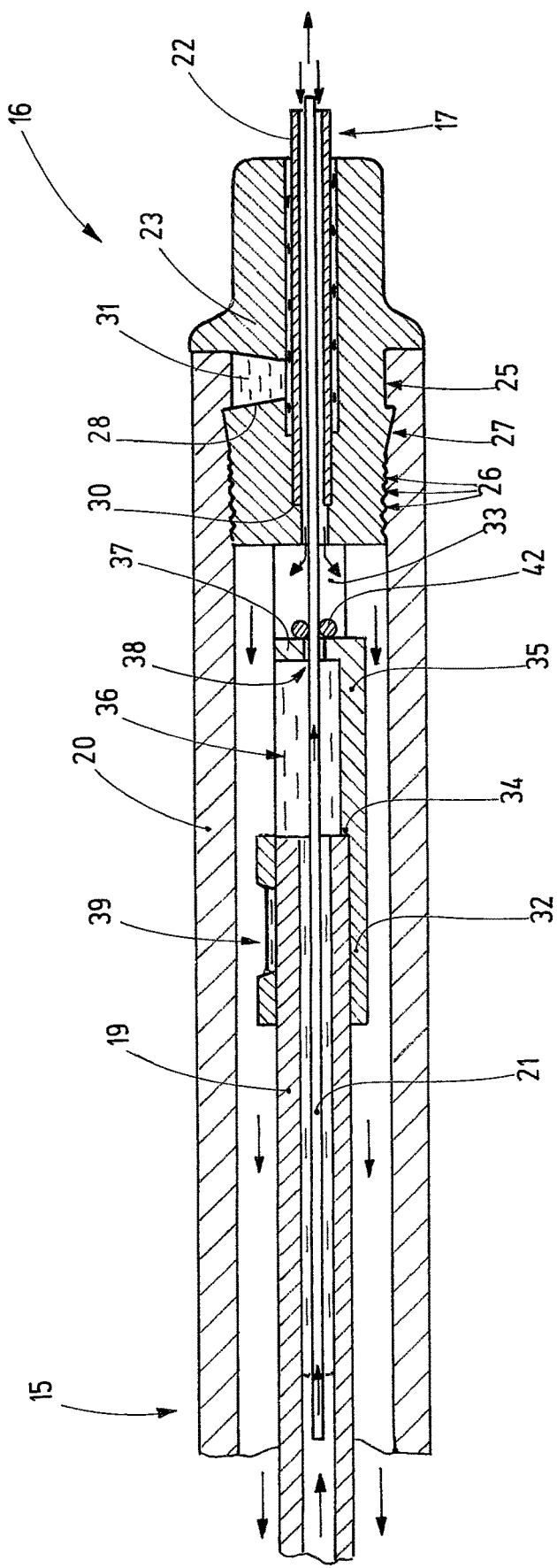
FIGS. 6 and 7 modified embodiments of the fluid connecting system according to the invention, each in longitudinal section.

FIG. 6 illustrates a modified embodiment of the fluid connecting system according to the invention to which applies the description hereinabove analogously. In addition, this embodiment has a barrier 42 located on the second inner line 21, said barrier being held on the inner line 21 in a friction-locked manner and, e.g., being formed by a rubber or plastic disk. During the joining process the barrier 42 comes into contact with the opening 38 and prevents the leakage of adhesive at that point during the gluing process. After the adhesive has cured, the barrier 42 does no longer have any function.

Figure 7:
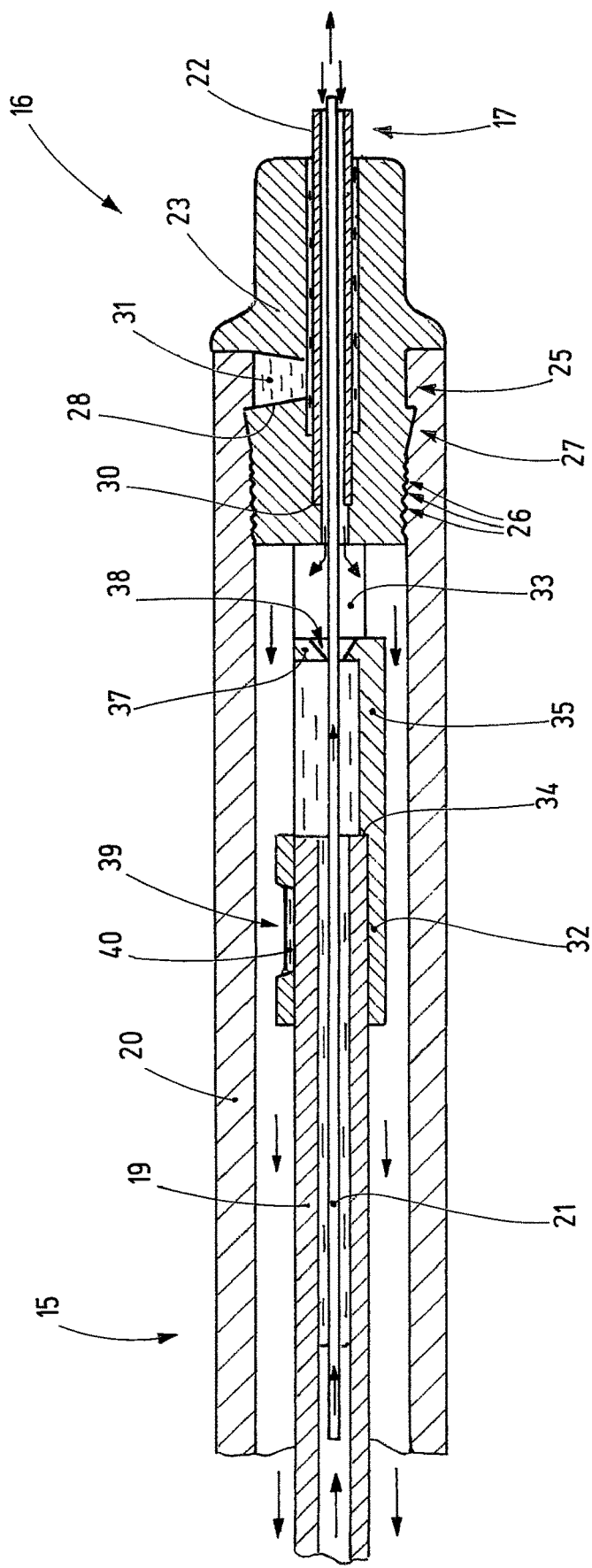

Another modified embodiment of the fluid connecting system is shown by FIG. 7. Also in this case the description hereinabove applies analogously. In addition, it applies that the opening 38 may be narrower than the annular shoulder 34 and also narrower than the passage opening 29. In particular, the opening 38 may be funnel-like, i.e., it may configured so as to widen conically toward the opening 29 in order to facilitate the insertion of the second inner line 21 into the connecting piece 16, on the one hand, and the handling of the gluing process, on the other hand.

Each of the fluid connecting systems described hereinabove comprises only a few (namely four) interfaces that need to be connected and sealed, this being preferably accomplished by planar bonding. The design only requires a minimal need of adaptation regarding the adaptation of dimensions and sizes of parts to each other. Furthermore, the connecting system according to the invention allows a quick assembly and minimal assembly effort. This leads to reduced product costs due to low costs for the necessary parts. Finally, the size and the weight of the connecting system are reduced. The invention allows the use of a simple sealing and connecting technique, in particular connection by gluing (e.g., by means of UV-cured adhesives, the utilization of the capillary effect for filling the adhesive gaps). Due to the connection and sealing by gluing, tolerances can be compensated for, which is why the parts that are used, in particular the inner lines 19, 21 and the outer lines 20, 22, are subject to lesser requirements regarding precision. For example, the inner lines 19, 21 may be pushed far apart in axial direction (e.g., several centimeters). As a result of this, the adhesive flow into the open end of the second inner line 21 is prevented even if the adhesive gap formed between the two inner lines 19, 21 is larger than would be ideal. Again, fewer parts are needed. Furthermore, due to the seal created by gluing, there are no parts needed, e.g., for pressing sealing elements. Likewise, separate sealing elements such as O-rings or the like can be omitted. By using the predefined adhesive well (adhesive reservoir), the gluing process can be automated and a reliable process ensured. With the use of the adhesive the gas supply is sealed relative to the gas return by up to 130 bar.

The use of plastics instead of metals allows lower parts and materials costs, in particular as a result of the use of injection-molded plastic parts.

List of Reference Signs:

| | |
|---|---|
| 10 | Cryoprobe |
| 11 | Fluid plug |
| 12, 13, 14 | Plug pins |
| 15 | First fluid conveying arrangement |
| 16 | Connecting piece/fluid connecting system |
| 17 | Second fluid conveying device |
| 18 | Cryo head |
| 19 | First inner line |
| 20 | First outer line |
| 21 | Second inner line |
| 22 | Second outer line |
| 23 | Outer line socket |
| 24 | Collar |
| 25 | Outer peripheral surface |
| 26 | Grooves |
| 27 | Rib |
| 28 | Radial passage |
| 29 | Axial passage opening |
| 30 | Step |
| 31 | Adhesive |
| 32 | Inner line socket |
| 33 | Spacer |
| 34 | Annular shoulder |
| 35 | Well section |
| 36 | Adhesive injection opening |
| 37 | Wall |
| 38 | Opening |
| 39 | Adhesive injection opening |
| 40, 41 | Adhesive |
| 42 | Barrier |

The invention claimed is:

1. A fluid connecting system (16) for connecting a first coaxial fluid conveying arrangement (15) to a second coaxial fluid conveying arrangement (17), the fluid connecting system comprising:
the first fluid conveying arrangement (15) having a first outside diameter and including a first inner line (19) and a first outer line (20) having an end which projects beyond an end of the first inner line (19),
the second fluid conveying arrangement (17) having a second outside diameter and including a second outer line (22) and a second inner line (21) having an end which projects beyond an end of the second outer line (22) and which extends into the first inner line (19) and is connected thereto,
wherein the ends of the two outer lines (20, 22) are connected to each other via an outer line socket (23) of a connecting piece (16),
wherein the outer line socket (23) has an outer peripheral surface (25) on which the first outer line (20) is held.

2. The fluid connecting system according to claim 1, wherein the first outer line (20) is glued to the outer peripheral surface (25) of the outer line socket (23).

3. The fluid connecting system according to claim 1, wherein the outer line socket (23) has an opening (29) in which the second outer line (22) is held.

4. The fluid connecting system according to claim 3, wherein the second outer line (22) is glued to an inner surface of the opening (29).

5. The fluid connecting system according to claim 1, wherein the outer line socket (23) has an opening (29) in which the second outer line (22) is held and a passage (28) that extends from the outer peripheral surface (25) to an inner surface of the opening (29).

6. The fluid connecting system according to claim 5, wherein the passage (28) is an adhesive reservoir (28).

7. The fluid connecting system according to claim 1, wherein the end of the second outer line (22) extends into the first outer line (20).

8. The fluid connecting system according to claim 1, wherein the first inner line (19) and the second inner line (21) are glued to each other.

9. The fluid connecting system according to claim 1, wherein the connecting piece (16) includes an inner line socket (32), in which the first inner line (19) is held.

10. The fluid connecting system according to claim 9, wherein the inner line socket (32) has a seat for the first inner line (19), whereby the seat has an adhesive filling opening

(39) that communicates with the outer surface of the first inner line (19) and is configured as a reservoir for adhesive.

11. The fluid connecting system according to claim 9, wherein the connecting piece (16) includes a spacer (33) which is connected to the inner line socket (32).

12. The fluid connecting system according to claim 1, wherein the connecting piece (16) includes an inner line socket (32) in which the second inner line (21) is held.

13. The fluid connecting system according to claim 12, wherein the inner line socket (32) includes an adhesive receiving space (35) through which the second inner line (21) extends and which communicates with the first inner line (19).

14. A cryoprobe (10) with a fluid connecting system according to claim 1.

15. A fluid connecting system (16) for connecting a first coaxial fluid conveying arrangement (15) to a second coaxial fluid conveying arrangement (17), the fluid connecting system comprising:
  the first fluid conveying arrangement (15) having a first outside diameter and including a first inner line (19) and a first outer line (20) having an end which projects beyond an end of the first inner line (19), and
  the second fluid conveying arrangement (17) having a second outside diameter and including a second outer line (22) and a second inner line (21) having an end which projects beyond an end of the second outer line (22) and which extends into the first inner line (19) and is connected thereto,
  wherein the ends of the two outer lines (20, 22) are connected to each other via an outer line socket (23) of a connecting piece (16),
  wherein the connecting piece (16) includes an inner line socket (32), in which the first inner line (19) is held.

16. The fluid connecting system according to claim 15, wherein the inner line socket (32) has a seat for the first inner line (19), whereby the seat has an adhesive filling opening (39) that communicates with the outer surface of the first inner line (19) and is configured as a reservoir for adhesive.

17. The fluid connecting system according to claim 15, wherein the outer line socket (23) has an opening (29) in which the second outer line (22) is held.

18. The fluid connecting system according to claim 15, wherein the connecting piece (16) includes a spacer (33) which is connected to the inner line socket (32).

19. A fluid connecting system (16) for connecting a first coaxial fluid conveying arrangement (15) to a second coaxial fluid conveying arrangement (17), the fluid connecting system comprising:
  the first fluid conveying arrangement (15) having a first outside diameter and including a first inner line (19) and a first outer line (20) having an end which projects beyond an end of the first inner line (19), and
  the second fluid conveying arrangement (17) having a second outside diameter and including a second outer line (22) and a second inner line (21) having an end which projects beyond an end of the second outer line (22) and which extends into the first inner line (19) and is connected thereto,
  wherein the ends of the two outer lines (20, 22) are connected to each other via an outer line socket (23) of a connecting piece (16),
  wherein the outer line socket (23) has an opening (29) in which the second outer line (22) is held,
  wherein the second outer line (22) is glued to an inner surface of the opening (29).

* * * * *